United States Patent [19]
Tanaka et al.

[11] Patent Number: 5,788,493
[45] Date of Patent: Aug. 4, 1998

[54] PERMANENT MAGNET ASSEMBLY, KEEPER AND MAGNETIC ATTACHMENT FOR DENTURE SUPPORTING

[75] Inventors: Kiyomi Tanaka, Kawamotomachi; Toru Sugihara, Kumagaya; Kazumi Noguchi, Kamikawamachi; Hiroya Suzuki, Kumagaya; Osamu Okuno, Sendai, all of Japan

[73] Assignee: Hitachi Metals, Ltd., Tokyo, Japan

[21] Appl. No.: 619,619

[22] PCT Filed: Jul. 14, 1995

[86] PCT No.: PCT/JP95/01404

§ 371 Date: Mar. 13, 1996

§ 102(e) Date: Mar. 13, 1996

[87] PCT Pub. No.: WO96/02206

PCT Pub. Date: Feb. 1, 1996

[30] Foreign Application Priority Data

Jul. 15, 1994 [JP] Japan ................. 6-163596

[51] Int. Cl.$^6$ ................................. A61C 13/235
[52] U.S. Cl. ................................. 433/189
[58] Field of Search ............... 433/189; 335/302, 335/304, 306

[56] References Cited

U.S. PATENT DOCUMENTS

| | | | |
|---|---|---|---|
| 4,815,975 | 3/1989 | Garrel et al. | 433/189 |
| 4,997,372 | 3/1991 | Shiner et al. | 433/189 |
| 5,123,843 | 6/1992 | Van Der Zel et al. | 433/189 |
| 5,254,006 | 10/1993 | Yamada | 433/189 |
| 5,337,033 | 8/1994 | Kinouchi et al. | 433/189 X |
| 5,421,722 | 6/1995 | Stemmann | 433/189 |
| 5,425,763 | 6/1995 | Stemmann | 433/189 X |

FOREIGN PATENT DOCUMENTS

| | | |
|---|---|---|
| 0 347 510 A1 | 12/1989 | European Pat. Off. |
| 62-211061 | 9/1987 | Japan . |
| 63-54157 | 3/1988 | Japan . |
| 2-295557 | 12/1990 | Japan . |
| 4-71551 | 3/1992 | Japan . |
| 5-95965 | 4/1993 | Japan . |
| 6-169936 | 6/1994 | Japan . |

OTHER PUBLICATIONS

Form PCT/ISA/210, (Oct. 24, 1995).

*Primary Examiner*—Nicholas D. Lucchesi
*Attorney, Agent, or Firm*—Finnegan, Henderson, Farabow, Garrett & Dunner, L.L.P.

[57] ABSTRACT

The invention relates to denture-supporting permanent magnet assemblies each using a magnetic attractive force, and provides denture-supporting permanent magnet assemblies, denture-supporting keepers, and denture-supporting magnetic attachments each of which uses a magnetic material with a high saturation magnetic flux density, i.e., a magnetic material comprising 15.5–18.5 wt % Cr and balance Fe as magnetic materials used for the permanent magnet assembly and the keeper in order to provide a magnetic attachment which keeps an excellent attractive force even if miniaturized.

Also disclosed are denture-supporting permanent magnet assemblies, denture-supporting keepers, and denture-supporting magnetic attachments in which a coating layer of Ti or a Ti compound is formed on the surface of each of the permanent magnet assemblies and denture-supporting keepers in order to enhance the safety of each magnetic attachment by means of raising the corrosion resistance while maintaining a practically sufficient attractive force.

16 Claims, 6 Drawing Sheets

PERMANENT MAGNET ASSEMBLY, KEEPER AND MAGNETIC ATTACHMENT FOR DENTURE SUPPORTING

TECHNICAL FIELD

The present invention relates to denture-supporting permanent magnet attachments which use magnetic attractive force and more particular to denture-supporting permanent magnet attachments which are used as retainers for retaining dentures and which each comprise a supporting plate comprising a magnetic stainless steel glued to the top surface of a coping laid in a tooth root and a permanent magnet assembly laid in a denture base.

BACKGROUND ART

There have already been various attempts to utilize magnetic attractive force interacting between a permanent magnet and a magnetic material alloy in settling a denture within an oral cavity. These attempts are described, for example, by Tomas R. Jackson in "The application of Rare Earth magnetic retention to osseointegrated implants," Int. J. Oral Maxillofac. Implants, Vol. 1, No. 2 (1987), pp. 77-89.

The requirements for putting this kind of dentures to practical use are thought to be that a permanent magnet is completely sealed up in a case made of materials which have been proved to be harmless to the human body and that leak of magnetic flux is small. There has been used, for example, a denture-supporting magnetic attachment having a structure shown in FIG. 3.

Figure 3:
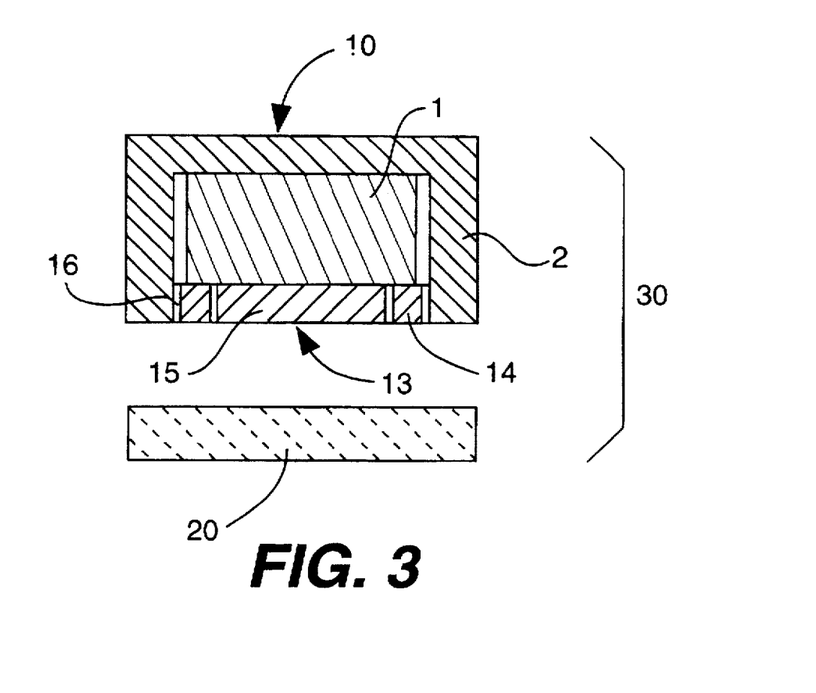
FIG. 3 is a section view of a conventional permanent magnet assembly.

FIG. 3 shows a denture-supporting magnetic attachment 30 comprising a permanent magnet assembly 10 and a keeper 20. In FIG. 3, reference numeral 1 denotes a permanent magnet, numeral 2 denotes a case, numeral 13 denotes a seal member. The seal member 13 comprises a seal frame member 14 and a seal center member 15, which are formed into a body by seam welding. Also, the seal member 13 and the case 2 are united in one by seam welding 16.

In this case, the case 2 is formed of (magnetic) ferritic stainless steel, e.g., SUS447J1 to be 4.4 mm in outer diameter, 3.23 mm in inner diameter, 2.1 mm in height and 1.60 mm in depth (0.50 mm in thickness of the bottom and the sides). The case 2 houses a SmCo-system magnet 1, 3.2 mm in outer diameter and 1.4 mm in height. On the other hand, the seal member 13 is formed into one body by seam-welding a seal center member made of (magnetic) ferritic stainless steel such as SUS447J1 and a seal frame member made of (nonmagnetic) austenitic stainless steel such as SUS316L (a). The seal member, which is made 3.2 mm in outer diameter, 2.7 mm in inner diameter and 0.21 mm in thickness, is fit into an open end of the case 2, and then seals up the permanent magnet 1 with seam welding 16.

(Translation Notes: A code with a prefix "SUS" indicates a stainless steel defined in Japanese Industrial Standard (JIS). The steel SUS447J1 contains in weight-%: 28.5-32.0 Cr, 1.5-2.5 Mo and balance iron. SUS316L contains in weight-%: 16-18 Cr, 12-15 Ni, 2-3 Mo and balance iron.)

In FIG. 3, the magnetic flux out of the permanent magnet 1 returns to the magnet via the case 2, the keeper 20 and the seal center member.

Figure 4:
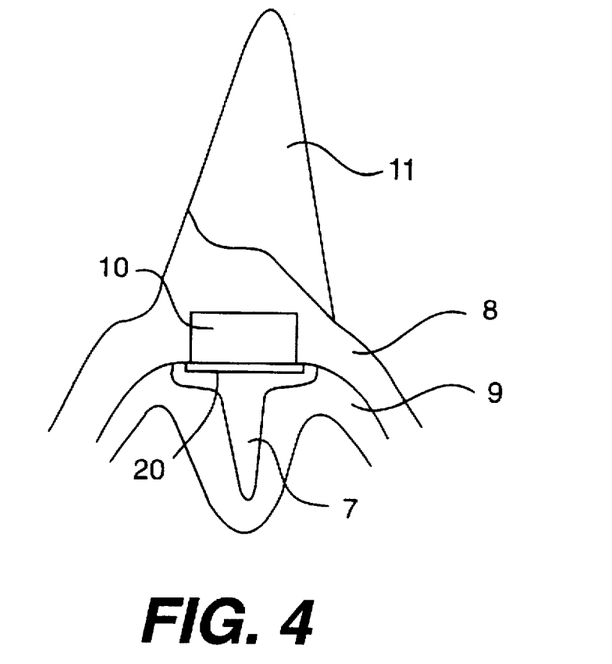
FIG. 4 is an illustrative diagram exemplifying how a magnetic-type denture retainer of the invention is used for denture supporting.

FIG. 4 is a partial section showing an exemplary denture-fixing means in which a conventional denture-supporting magnetic attachment is used. In FIG. 4, reference numeral 7 denotes a root member lied in a tooth root 9, which is provided with a keeper 20 formed of magnetic material stainless steel on its top surface and which has a longitudinal section of a substantial T-shape. Reference numeral 8 denotes a denture base, in which the permanent magnet assembly 10 shown in FIG. 3 is placed with its seal member 13 side facing the root member 7. The above described arrangement will produce a magnetic attractive force between the permanent magnet assembly 10 and the root member 7, which causes the denture base 8 to be pressed against the tooth root 9, thereby enabling the artificial teeth 11 to be supported within the oral cavity.

Figure 5:
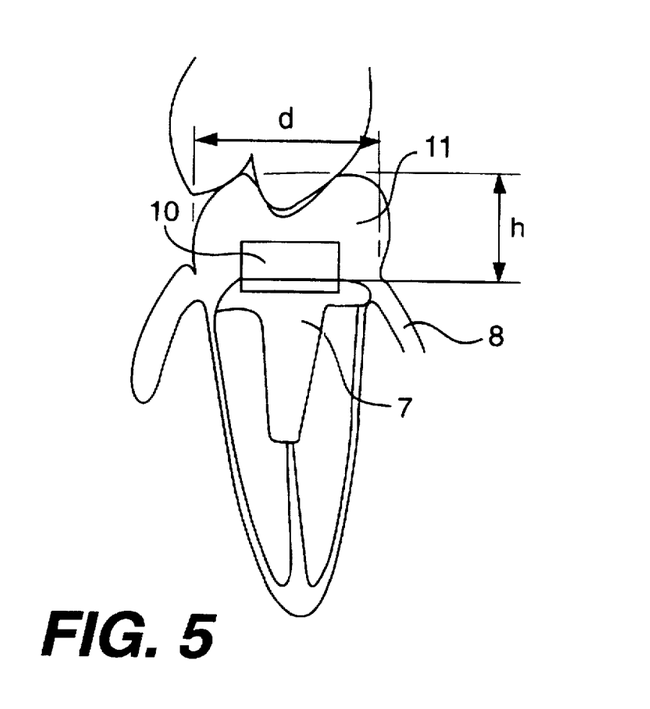
FIG. 5 is a section view for explaining a lacuna necessary for embedding a magnet assembly in a molar-corresponding part.

The permanent magnet assembly 10 arranged as described above have been used as follows. As shown in FIG. 5, a denture base and artificial teeth 11 are disposed as a denture in a space where the coronae dentis of natural teeth used to be, and a permanent magnet assembly 10 is embedded in the denture base 10. In case of a molar shown in FIG. 5, the vertical lacuna between the root member 7 and the engaging tooth, "h", is about 4.0 mm, and the horizontal lacuna "d" or the minimum length of the cervix dentis is about 5.5 mm. In such a limited lacuna, there is now used a permanent magnet assembly with a diameter of 4.0 mm and a thickness of 2.1 mm as one which has a size as small as possible while keeping its attractive force more than 250 gf. However, the miniaturization of permanent magnet assembly 10 is required in order to use a dental prothesis without feeling a malaise.

However, in a conventional permanent magnet assembly, the case and the seal center member which are made of magnetic material alloy have a saturation magnetic flux density Bs as small as 9 KG, and the used permanent magnet, which is a SmCo magnet, has a remanent magnetic flux density Br of 9 KG, so that there is a problem that miniaturizing a permanent magnet assembly results in a lowering of attractive force of the assembly.

Further, though the permanent magnet assembly is embedded as shown in FIG. 5, the seal member 15 and the case 2 which are shown in FIG. 3 and face the root member 7 are uncovered. Certain kinds of stainless steels (Fe—Ni—Cr alloys) and Co—Cr—Mo alloys are credited with a possibility of causing a metallic allergy due to Ni or Co. Ti—Ni alloys and Ti—6Al—4V alloys are at least admitted as medical metal materials by the Welfare Ministry (in Japan) and FDA (in U.S.) respectively, whereas, considering allergies to Ni among others, the three Scandinavian countries are prohibiting the use of the alloys containing 0.9% or more Ni as a medical material.

The first object of the invention is to solve these and other problems of the prior art and provide a denture-supporting permanent magnet assembly which has such a small size as permit its embedding in the above described h×d lacuna with a sufficient allowance, which has a structure preventing metal ions from dissolving out, and which has a attractive force appropriate for retaining a denture. The second object of the invention is to provide a denture-supporting permanent magnet assembly and a denture-supporting keeper with an excellent corrosion resistance, and a denture-supporting magnetic attachment making use of them.

DISCLOSURE OF THE INVENTION

A denture-supporting permanent magnet assembly according to one aspect of the invention is characterized in that: the assembly comprises a case formed of a magnetic material and having an opening at one end, a permanent magnet housed in the case, and a seal member which has a magnetic part and a nonmagnetic part and which seals up the open end of the case; and the case uses a corrosion-resistant magnetic material with a high saturation magnetic flux density, that is, a corrosion-resistant magnetic material containing Cr and Fe.

Also, the seal member can be formed of a seal frame member made of a nonmagnetic material and a seal center member made of a corrosion-resistant magnetic material which contains Cr and Fe as the case does.

Further, it yields a more excellent corrosion resistance to form a coating layer of Ti and/or a Ti compound on the surface of the denture-supporting permanent magnet assembly.

A denture-supporting permanent magnet assembly according to another aspect of the invention comprises a case formed of a magnetic or nonmagnetic material and having an opening at one end, a permanent magnet housed in the case, and a seal member for sealing up the open end of the case, and has a coating layer of Ti or a Ti compound on the surface.

A denture-supporting permanent magnet assembly according to still another aspect of the invention comprises a case formed of a magnetic or nonmagnetic material and having an opening at one end, a permanent magnet housed in the case, and a seal member for sealing up the open end of the case, the case being crowned with a Ti-system case made of Ti or a Ti compound.

Also, a denture-supporting permanent magnet assembly according to further aspect of the invention employs an Nd—Fe—B system magnet with a high remanent magnetic flux density as the permanent magnet.

A denture-supporting keeper according to one aspect of the invention has a coating layer of Ti or a Ti compound on the surface of the body of the keeper.

A denture-supporting keeper according to another aspect of the invention has a coating layer of Ti or a Ti compound on the surface of the body of the keeper, and is provided with a handle of Ti or a Ti compound.

A denture-supporting magnetic attachment according to the invention comprises: a denture-supporting permanent magnet assembly comprising a case formed of a magnetic or nonmagnetic material and having an opening at one end, a permanent magnet housed in the case, and a seal member for sealing up the open end of the case; and a denture-supporting keeper formed of a magnetic material, and is characterized in that the denture-supporting permanent magnet assembly has a coating layer of Ti or a Ti compound on the surface.

As described above, the invention provides magnetic attachments each retaining an excellent attractive force even when miniaturized, by using a corrosion-resistant magnetic material with a high saturation magnetic flux density as a magnetic material used for the permanent magnet assembly and the keeper. Additionally, the permanent magnet assembly and the keeper are coated with Ti or a Ti compound so as to enhance the corrosion-resistance while maintaining a practically sufficient attractive force for raising the safety of the magnetic attachment consisting thereof.

EXPLANATION OF REFERENCE NUMERALS

1: permanent magnet
2: case
8: denture base
10: denture-supporting permanent magnet assembly
11: artificial teeth
13: seal member
14: seal frame member
15: seal center member
20: keeper
22: handle
30: denture-supporting magnetic attachment

BEST MODE FOR CARRYING OUT THE INVENTION

In a denture-supporting permanent magnet assembly of the invention, the case and/or the seal member is formed of a corrosion-resistant magnetic material either containing 15.5–18.5 wt % Cr and balance iron, or containing in weight-%: 15.5–18.5 Cr, 0.05–1.5 Mo and balance iron.

If the chromium content in the corrosion-resistant magnetic material is less than 15.5 wt %, the corrosion-resistance will become insufficient. On the other hand, a more than 18.5 wt % chromium content will result in a lowering of the saturation magnetic flux density Bs and accordingly a degradation in the attractive force. It is noted that molybdenum can be added in a range of 0.05–1.5 wt % in order to raise the corrosion-resistance.

The seal member, which comprises magnetic and nonmagnetic parts, may be realized either by using a compound magnetic member which has both magnetism and nonmagnetism, or by joining a magnetic and nonmagnetic members together.

Though the corrosion-resistant magnetic material according to the invention is 1.3 T or more in saturation magnetic flux density Bs, making the saturation magnetic flux density Bs more than 1.5 T will yields a stronger attractive force.

In order to enhance the corrosion-resistance in a denture-supporting permanent magnet assembly of the invention, it is preferable to always restrain C, Si or Mn from mixing in a permanent magnet alloy in the manufacturing process. That is, the C, Si and Mn contents are preferably 0.2 or less, 0.50 or less and 0.50 or less, respectively, in weight percentage. Particularly, since carbon constitutes carbides from which a corrosion may originate, the carbon content is more preferably less than 0.1 wt %.

A permanent magnet assembly using a case and a seal center member which are formed of a corrosion-resistant magnetic material according to the invention has an excellent corrosion resistance. However, a further excellent corrosion-resistance can be obtained by forming a coating layer of Ti or a Ti compound having excellent stability and high corrosion-resistance on the surface of the permanent magnet assembly.

TiN, TiC and TiCN are preferable as a Ti compound.

If the thickness of the coating layer is less than 1 micrometers, the corrosion-resistance is not sufficiently raised because the coating layer is difficult to form uniformly. If the thickness exceeds 20 micrometers, the attractive force of the magnet assembly lowers. Therefore, the thickness of the coating layer is desirably 1 to 20 micrometers, preferably 1 to 10 micrometers. If a stronger attractive force is required, 7 micrometers or less is preferred. Also, more than two coating layers of Ti or a Ti compound may be formed one over another, in which case the whole thickness of the coating layers has to be 1 to 20 micrometers.

Since among the sides of the permanent magnet assembly, those other than the side facing the keeper are covered with the denture base, a coating layer which is formed on the keeper-facing side of the permanent magnet assembly would have a sufficient effect of enhancing the corrosion-resistance. However, coating all over the surface of the permanent magnet assembly is preferable in order to prevent the coating layer from pealing off.

A coating layer of Ti or a Ti compound can be formed by means of ion plating at a temperature of 150° to 500° C. and a vacuum degree of $10^{-2}$ to $10^{-5}$ Torr for 0.5 to 40 minutes. It is desirable to clean the surface of the permanent magnet assembly in an alkaline solution having a pH of 12–14 for 10 to 40 minutes before forming a coating layer, the cleaning is preferably achieved by ultrasonic cleaning. Alternatively, a coating layer of Ti or a Ti compound may be formed by means of any of PVD methods such as conventional vacuum evaporation and sputtering, and CVD methods.

Further, according to one aspect of the invention, the corrosion-resistance of a permanent magnet assembly can be raised by crowning the magnetic or nonmagnetic material case of the permanent magnet assembly with a case formed of Ti or a Ti compound.

Figure 6:
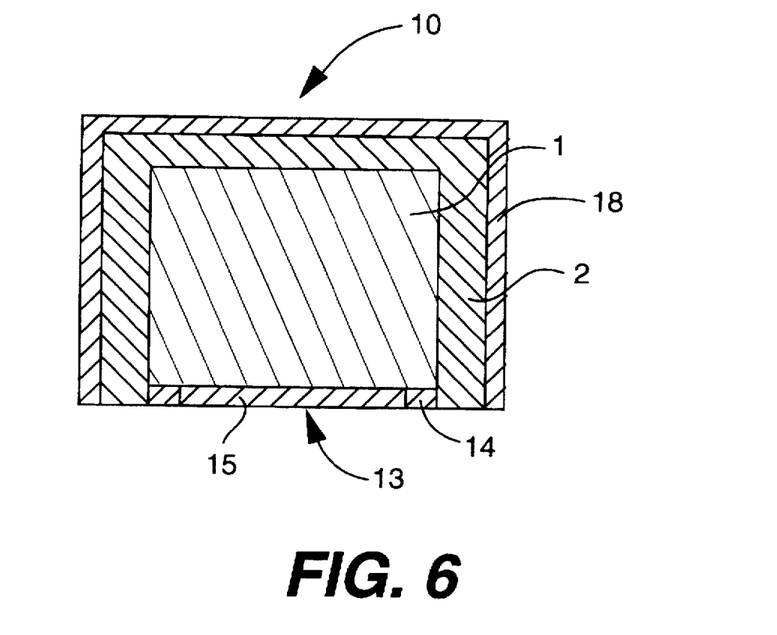
FIG. 6 is a section view of a permanent magnet assembly of the invention.

FIG. 6 is a permanent magnet assembly crowned with a case of Ti material. In FIG. 6, reference numeral 2 denotes a case formed of a magnetic material and having an opening at one end, numeral 1 denotes a permanent magnet housed in the case, 13 denotes a seal member comprising a seal frame member 14 and a seal center member 15 to seal up the open end of the case, 18 denotes a case of Ti material which covers the case 2.

In order to miniaturize a permanent magnet assembly, it is preferable to use a magnet with a remanent magnetic flux density Br of 1.0 T or more. As such a magnet, a magnet of Nd—Fe—B system can be used.

Since the Nd—Fe—B system magnets contains a rare earth element such neodymium which is easy to oxidize, it is preferred to form a corrosion-resistant film 10 to 40 micrometers thick on the magnet surface to raise the corrosion resistance. The corrosion-resistant film may be either any of single-layer films formed by coating with resin, electrolytic plating with Ni, Cu, etc., electroless plating with Ni—P etc., and coating with metal, or a compound film comprising these films.

A denture-supporting keeper of the invention has a function of retaining a magnet assembly with a magnetically attracting force working with the magnet assembly. In order to make effective use of an excellent attractive force of an inventive magnet assembly, it is desirable to use a material with a saturation magnetic flux density Bs of 1.3 T or more.

preferably 1.5 T or more, as a magnetic material forming a keeper. As is the case with a case of a permanent magnet assembly, it is preferable to use, as such a material, a corrosion-resistant magnetic material either containing 15.5–18.5 wt % Cr and balance iron, or containing in weight-%: 15.5–18.5 Cr, 0.05–1.5 Mo and balance iron. Further, a keeper with a high corrosion resistance can be obtained by forming a coating layer of Ti or a Ti compound on the surface of the keeper. Though it may be sufficient to formed a coating layer only on at least the side of a keeper which faces the permanent magnet assembly, coating all over the surface of the keeper is preferable in order to prevent the coating layer from pealing off. Also, as is the case with a permanent magnet assembly, the coating layer for a keeper is desirably formed to 1 to 20 micrometers, preferably 1 to 10 micrometers, in thickness.

A keeper of the invention is preferably provided with a handle for use in fixing the keeper within a mold at the time of casting-in of a keeper and a coping in a lost wax process. Providing a keeper with such a handle facilitates its handling in using the keeper in a dental office. The handle is preferably formed of Ti or a Ti compound.

Figure 7:
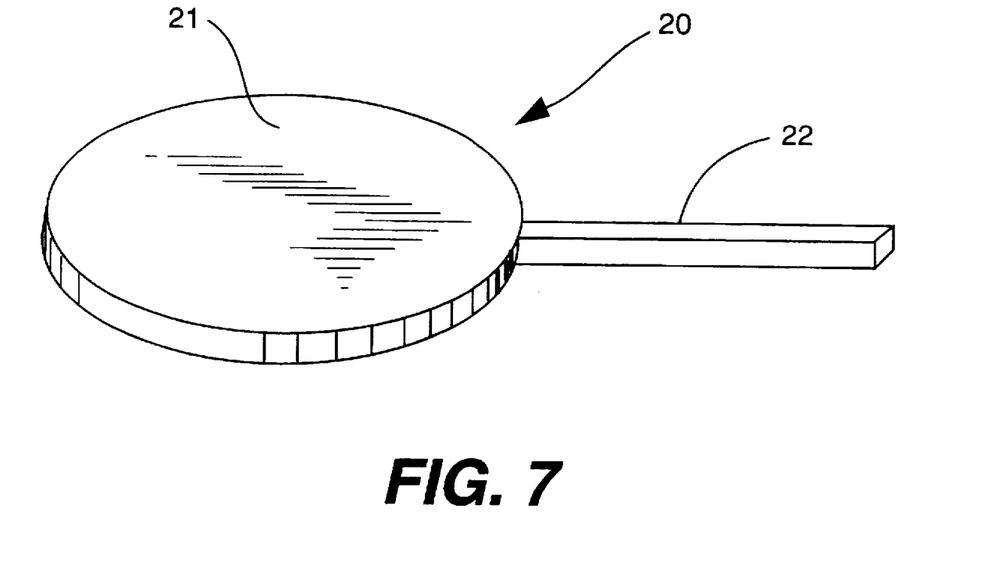
FIG. 7 is a schematic diagram of a denture-supporting keeper of the invention.

FIG. 7 shows a denture-supporting keeper having a handle. In FIG. 7, reference numeral 21 denotes a keeper part or the keeper main body formed of a magnetic material, the surface of which is coated with Ti or a Ti compound. Numeral 22 is a handle part formed of Ti or a Ti compound.

Figure 8A:
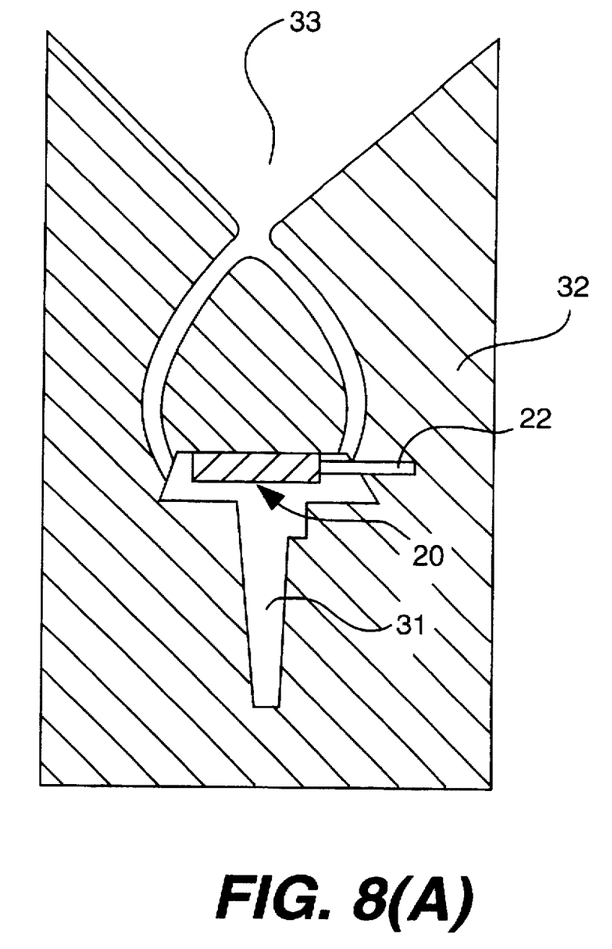
FIG. 8 is a diagram showing a cast-in system according to the lost wax process for a coping and an inventive denture-supporting keeper and the state of an article having been casted.

We now describe the casting-in of a keeper with a coping by means of a lost wax process referring to FIG. 8(A). In FIG. 8(A), reference numeral 31 denotes a wax pattern having a shape of a coping, 32 denotes a investing material. A keeper 20 having a handle 22 is disposed in a predetermined position of the wax pattern 31, and the wax pattern and keeper is buried with and in the investing material 32 for molding. The handle 22 of the keeper 20 is so fixed in the wax pattern that the keeper will not move within the mold when the wax pattern is dewaxed. After dewaxing the wax pattern, molten metal is poured from a sprue 33 to cast a coping, casting-in the keeper at the same time.

Figure 8B:
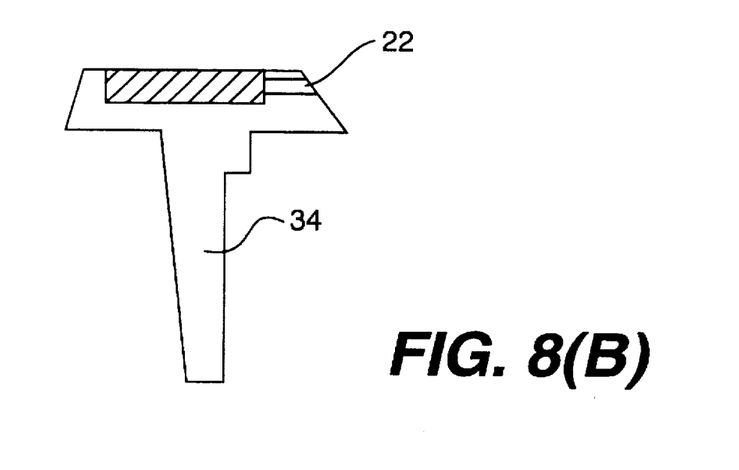

After the keeper has been cast in to the coping 34 by using a keeper having a handle, a part of the handle which is projecting from the coping is cut off. That is, a part of the handle remains in the coping 34 as shown in FIG. 8(B). Forming the handle out of Ti or a Ti compound causes the corrosion resistance to be raised further because the section of the handle and the joining interface between the keeper itself and the handle are never exposed.

Also, a denture-supporting permanent magnet assembly according to the invention and a denture-supporting magnetic attachment utilizing the assembly, a denture-supporting permanent magnet assembly with Ti coating on the surface and a denture-supporting magnetic attachment utilizing the just mentioned assembly, and a denture-supporting permanent magnet assembly crowned with a Ti case and a denture-supporting magnetic attachment utilizing the last mentioned assembly can be applied to permanent magnet assemblies of various structures to raising their corrosion resistances. They are also applicable to, e.g., (a) sandwich type permanent magnet assemblies and (b) split-pole type permanent magnet assemblies as shown in FIG. 9.

Figure 9A:
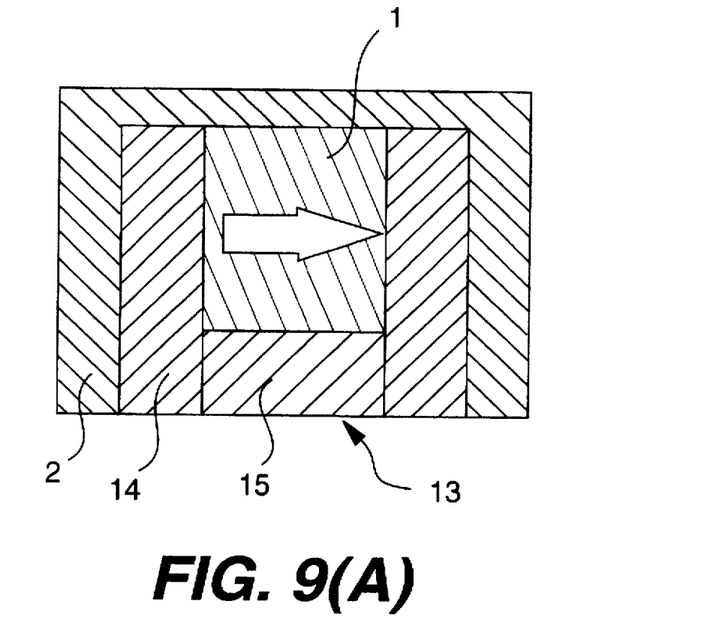
FIG. 9 is a section view showing embodiments of denture-supporting permanent magnet assemblies of the invention.

FIG. 9(a) shows a sandwich type permanent magnet assembly, which comprises a permanent magnet 1, a case 2 and a seal member 13. The seal member 13 is formed of a seal frame member 14 formed of a magnetic material and a seal center member 15 formed of a nonmagnetic material. In FIG. 9(a), the case 2 is formed of a nonmagnetic material, and the permanent magnet is magnetized in the direction parallel to the seal center member 15 (The magnetization direction is shown with an arrow).

Figure 9B:
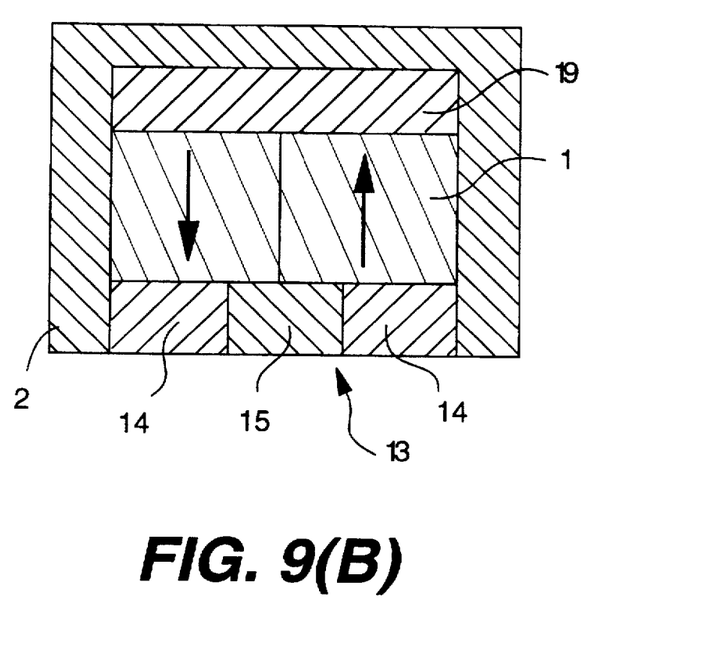

FIG. 9(b) shows a split-pole type permanent magnet assembly, which comprises permanent magnets 1, a case 2, a seal member 13 and a york 19. The seal member 13 is formed of a seal frame member 14 formed of a magnetic material and a seal center member 15 formed of a nonmagnetic material. Generally speaking, the case is formed of a nonmagnetic material, and the york 19 is formed of a magnetic material in FIG. (b). The permanent magnets 1 are magnetized in the directions opposite to each other and perpendicular to the seal center member 15 (The magnetization directions are shown with arrows).

EMBODIMENTS

We specifically describe effects of denture-supporting permanent magnet assemblies and denture-supporting magnetic attachments of the invention on the basis of preferred embodiments in the following.

We have made, by way of experiment, various permanent magnet assemblies of 3.0 to 4.5 mm in diameter and 1.0 to 1.6 mm in thickness. The target attractive force was set for 370 to 910 gf, which is the minimum attractive force necessary for molars and the attractive force against which even a tooth affected with myelopathy will remain undrawn.

Figure 1:
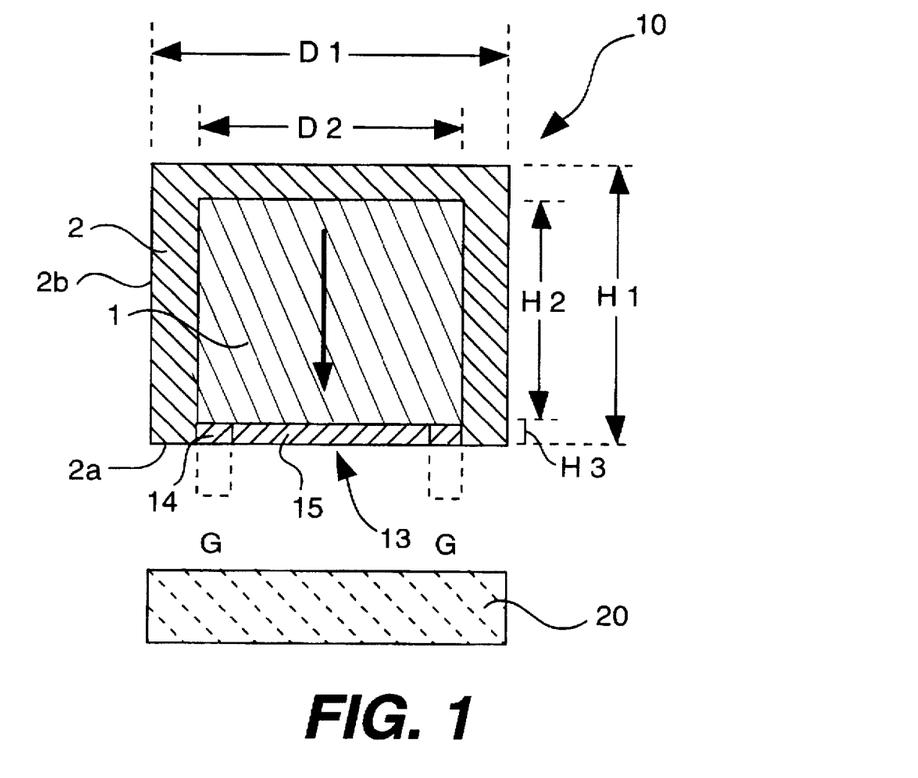
FIG. 1 is a schematic section view showing a structure of an embodiment of the invention.

FIG. 1 is a section view of a denture-supporting permanent magnet assembly comprising a case 2 formed of a magnetic material and having an opening at one end, a permanent magnet 1 housed in the case, and a seal member 13 for sealing up the open end of the case. The seal member 13 comprises a seal frame member 14 formed of a nonmagnetic material and a seal center member 15 formed of a magnetic material with the latter fitted in the former. The seam between the case 2 and the seal member 13 which have been assembled together and the seam between the seal frame member 14 and the seal center member 15 are joined by laser welding.

In the following first through fourth illustrative embodiments, permanent magnet assemblies have been made varying the diameter D2 and the thickness H2 of the permanent magnet, the outer diameter D1 and the thickness H1 of the case 2, the thickness H3 of the seal member, and the width G of the seal frame member shown in FIG. 1, and then the attractive force in each case has been evaluated.

In the following fifth through ninth illustrative embodiments, a coating layer of Ti or a Ti compound has been formed on the surface of the permanent magnet assembly shown in FIG. 1, and the corrosion resistance, the wear resistance and the clingingness of the coating layer has been evaluated.

(Embodiment 1)

A permanent magnet assembly was made in the following way: an Nd—Fe—B magnet 1 (the remanent magnetic flux density Br=13 KG, the coercive force iHc=15 KOe) was worked to 3.46 mm in diameter D2 and 0.7 mm in thickness H2; epoxy-coated to 25 micrometers in thickness; magnetized in the direction shown with an arrow; inserted in a case 2 formed of ferritic stainless steel SUS430 (a magnetic material: 17.7 Cr and balance Fe) and having an outer diameter D1 of 4.5 mm and a thickness of 1.52 mm; and then covered with a seal member 13 made by fitting a seal center member 15 formed of the same material as that of the case and having a thickness H3 of 0.21 mm in a seal frame member 14 of austenitic stainless steel SUS316L (nonmagnetic material). The saturation magnetic flux density Bs of SUS430 is 16 KG, and the width G of the seal frame member is 0.25 mm. Grinding for bead removal resulted in H1=1.5 mm. Defining the attractive force as the force which, when a permanent magnet assembly is made to absorb a keeper formed of the same material as that of the case and having a diameter of 4.5 mm and a thickness of 0.8 mm, is necessary for pulling the keeper perpendicularly apart from the permanent magnet assembly, we have measured the attractive force of the permanent magnet assembly with a diameter D1 of 4.5 mm according to the invention, and found it to be 910 gf.

(Prior Art Example 1)

A permanent magnet assembly was made in the same way as that of the first embodiment except that the permanent magnet was an SmCo$_5$ magnet (the remanent magnetic flux density Br=9.5 KG, the coercive force iHC=14 KOe), a ferrite stainless steel SUS447J1 (the saturation magnetic flux density Bs=12 KG) was used for the materials of the case and the seal center member, and G=0.25 mm. The permanent magnet assembly was made to absorb a keeper formed of the same material as that of the case 2 and having a diameter of 4.5 mm and a thickness of 1.0 mm, the attractive force was measured and found to be 440 gf. Therefore, the attractive force of the first embodiment or an inventive example is approximately twice that of the first prior art example.

(Embodiment 2)

A permanent magnet assembly was made in the following way: an Nd—Fe—B magnet 1 (the remanent magnetic flux density Br=13 KG, the coercive force iHc=15 KOe) was worked to 3.06 mm in diameter D2 and 0.7 mm in thickness H2; epoxy-coated to 20 micrometers in thickness; magnetized in the direction shown with an arrow; inserted in a case 2 formed of ferritic stainless steel SUS430 (the saturation magnetic flux density Bs=16 KG) and having an outer diameter D1 of 4.0 mm and a thickness of 1.52 mm; and then covered with a seal member 13 made by fitting a seal center member 15 formed of the same material as that of the case and having a thickness H3 of 0.21 mm in a seal frame member 14 of austenitic stainless steel SUS316L. The width G of the seal frame member was 0.25 mm. Grinding for bead removal resulted in H1=1.5 mm. Defining the attractive force as the force which, when a permanent magnet assembly is made to absorb a keeper formed of the same material as that of the case 2 and having a diameter of 4.0 mm and a thickness of 0.8 mm, is necessary for pulling the keeper perpendicularly apart from the permanent magnet assembly, we have measured the attractive force of the permanent magnet assembly with a diameter D1 of 4.0 mm according to the invention, and found it to be 720 gf.

(Prior Art Example 2)

A permanent magnet assembly was made in the same way as that of the second embodiment except that the permanent magnet was an SmCo$_5$ magnet (the remanent magnetic flux density Br=9.5 KG, the coercive force iHC=14 KOe), a ferrite stainless steel SUS447J1 (the saturation magnetic flux density Bs=12 KG) was used for the materials of the case and the seal center member, and G=0.25 mm. The permanent magnet assembly was made to absorb a keeper formed of the same material as that of the case 2 and having a diameter of 4.0 mm and a thickness of 1.0 mm, the attractive force was measured and found to be 387 gf. Therefore, the attractive force of the second embodiment or an inventive example is approximately 1.9 times that of the second prior art example.

(Embodiment 3)

A permanent magnet assembly was made in the following way: an Nd—Fe—B magnet 1 (the remanent magnetic flux density Br=13 KG, the coercive force iHc=15 KOe) was worked to 2.70 mm in diameter D2 and 0.7 mm in thickness H2; plated with nickel to 25 micrometers in thickness; magnetized in the direction shown with an arrow; inserted in a case 2 formed of ferritic stainless steel SUS430 (the saturation magnetic flux density Bs=16 KG) and having an outer diameter D1 of 3.5 mm and a thickness of 1.52 mm; and then covered with a seal member 13 made by fitting a seal center member 15 formed of the same material as that of the case and having a thickness H3 of 0.21 mm in a seal frame member 14 of austenitic stainless steel SUS316L. The width G of the seal frame member was 0.25 mm. Grinding for bead removal resulted in H1=1.5 mm. Defining the attractive force as the force which, when a permanent magnet assembly is made to absorb a keeper formed of the same material as that of the case 2 and having a diameter of 3.5 mm and a thickness of 0.8 mm, is necessary for pulling the keeper perpendicularly apart from the permanent magnet assembly, we have measured the attractive force of the permanent magnet assembly according to the invention, and found it to be 530 gf.

(Prior Art Example 3)

A permanent magnet assembly was made in the same way as that of the third embodiment except that the permanent magnet was an SmCo$_5$ magnet (the remanent magnetic flux density Br=9.5 KG, the coercive force iHC=14 KOe), a ferrite stainless steel SUS447J1 (the saturation magnetic flux density Bs=12 KG) was used for the materials of the case and the seal center member, and G=0.25 mm. The permanent magnet assembly was made to absorb a keeper formed of the same material as that of the case 2 and having a diameter of 3.5 mm and a thickness of 1.0 mm, the attractive force was measured and found to be 288 gf. Therefore, the attractive force of the third embodiment or an inventive example is approximately 1.8 times that of the third prior art example.

(Embodiment 4)

A permanent magnet assembly was made in the following way: an Nd—Fe—B magnet 1 (the remanent magnetic flux density Br=13 KG, the coercive force iHc=15 KOe) was worked to 2.32 mm in diameter D2 and 0.7 mm in thickness H2; plated with nickel to 20 micrometers in thickness; magnetized in the direction shown with an arrow; inserted in a case 2 formed of ferritic stainless steel SUS430 (the saturation magnetic flux density Bs=16 KG) and having an outer diameter D1 of 3.0 mm and a thickness of 1.52 mm; and then covered with a seal member 13 made by fitting a seal center member 15 formed of the same material as that of the case and having a thickness H3 of 0.21 mm in a seal frame member 14 of austenitic stainless steel SUS316L. The width G of the seal frame member was 0.25 mm. Grinding for bead removal resulted in H1=1.5 mm. Defining the attractive force as the force which, when a permanent magnet assembly is made to absorb a keeper formed of the same material as that of the case 2 and having a diameter of 3.0 mm and a thickness of 0.8 mm, is necessary for pulling the keeper perpendicularly apart from the permanent magnet assembly, we have measured the attractive force of the permanent magnet assembly with a diameter D1 of 3.0 mm according to the invention, and found it to be 370 gf.

(Prior Art Example 4)

A permanent magnet assembly was made in the same way as that of the fourth embodiment except that the permanent magnet was an SmCo$_5$ magnet (the remanent magnetic flux density Br=9.5 KG, the coercive force iHC=14 KOe), a ferrite stainless steel SUS447J1 (the saturation magnetic flux density Bs=12 KG) was used for the materials of the case and the seal center member, and G=0.25 mm. The permanent magnet assembly was made to absorb a keeper formed of the same material as that of the case 2 and having a diameter of 3.0 mm and a thickness of 1.0 mm, the attractive force was measured and found to be 190 gf. Therefore, the attractive force of the fourth embodiment or an inventive example is approximately 1.9 times that of the fourth prior art example.

Figure 2:
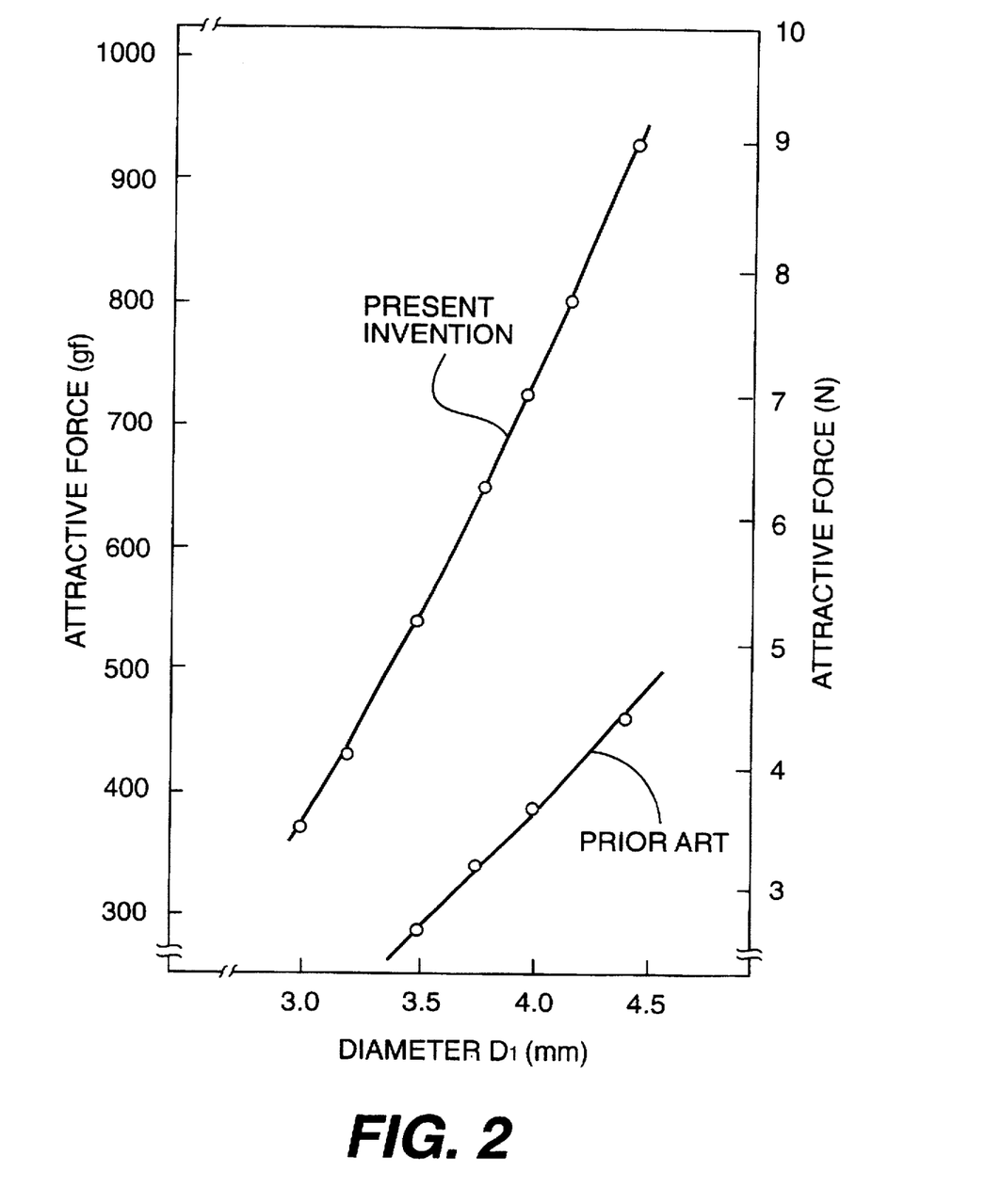
FIG. 2 is a diagram showing a relationship between the diameter D1 and the attractive force with respective to permanent magnet assemblies of the present invention and the prior art.

The relationship between the diameter D1 and the attractive force of the permanent magnet assemblies of Embodiments 1 through 4 is shown in FIG. 2.

As is seen from FIG. 2, a permanent magnet assembly of the invention has a remarkably increased attractive force as compared with a conventional one, so that the inventive permanent magnet assembly, even if miniaturized, can provide an attractive force equal to or more than that the conventional one provides.

(Embodiment 5)

Nd—Fe—B magnets 1 (the remanent magnetic flux density Br=13 KG, the coercive force iHc=15 KOe) were worked to 3.46 mm in diameter D and 0.7 mm in thickness H2; epoxy-coated to 20 micrometers in thickness; inserted in a case 2 formed of ferrite stainless steel SUS430 and having an outer diameter D1 of 4.5 mm and a thickness H2 of 1.52 mm; and then covered with a seal member 13 made by fitting a seal center member 15 formed of the same material as that of the case and having a thickness H2 of 0.21 mm in a seal frame member 14 of austenitic stainless steel SUS316L. The width G of the seal frame members were 0.25 mm. The resultant magnet assemblies in which grinding for bead removal had resulted in H1=1.5 mm were degreased in an alkaline solution having a pH of 12–14 for 20 as a preparatory process. Then, single-layer coating layers referred to as Nos. A through D, Y and Z as shown in the first table were formed by means of ion plating at a temperature of 200° to 250° C. and a vacuum degree of $5 \times 10^{-4}$ Torr for 5 to 15 minutes. The coating layers were formed to 2.5 micrometers in thickness on all over the surface of the magnet assemblies. Following the coating layer formation, the magnet assemblies were magnetized in the arrow direction, thus permanent magnet assemblies being obtained.

Each of the permanent magnet assemblies was made to absorb a keeper formed of the same material as that of the case 2 and having a diameter of 4.5 mm and a thickness of 0.8 mm; the force necessary for pulling the keeper perpendicularly apart from the permanent magnet assembly was measured defining the force as the attractive force; and the attractive force of any permanent magnet assembly with a coating layer was found to be 870 gf.

In order to evaluate the corrosion resistance of each of the above mentioned permanent magnet assemblies, a test was made using a physiological saline as the test solution at a test temperature of 37° C. for a test time of 240 hours, and the surface conditions before and after the test was compared by using an optical microscope. Each of Embodiments A, . . . , D, X, exhibited a good corrosion resistance. Then, In order to further evaluate the corrosion resistance, the permanent magnet assemblies were soaked in a solution of 6% FeCl$_3$+ N/20HCl at a test temperature of 35° C. for a time of 24 hours, and dissolved ions were measured to evaluated the degree of corrosion resistance. Assuming the degree of corrosion resistance in case of "no coating" (No. X) to be one, the degrees of corrosion resistance for Embodiments A through D are shown in Table 1, where the larger the degree of corrosion resistance is, the better the corrosion resistance is.

Furthermore, the wear resistance is evaluated by applying a pressure of 10 kg to a central part of a seal member with a sapphire ball 10 mm in diameter 106 times, and measuring the depth of the mark made by wearing. The evaluation of the clingingness of the coating layer to the base material of each permanent magnet assembly was made through a peel test. Specifically, a pulling jig was glued to the attractive side of each of the coated permanent magnet assemblies with a commercially available dental adhesive "Super-Bond", whether the attractive side was peeled was observed pulling the pulling jig perpendicularly to the attractive side.

As seen from Table 1, Embodiments A through D showed no change in the surface condition in the corrosion resistance test using physiological saline to give better results as compared with Reference Examples Y and Z, which gathered rust. It is found from the comparison of the degrees of corrosion resistance that the corrosion resistance had been remarkably risen by forming a coating layer Ti or a Ti compound. The evaluation of the wear resistance is such that Embodiments A through D showed much smaller wear as compared with Reference Examples Y and Z. As for the clingingness of a coating layer, Reference Examples Y and Z let their coating layer peel, while any of the Embodiments showed such a sufficient clinging force as to cause a peel to occur at the interface between the adhesive and the coating layer.

TABLE 1

| | No. | Coating Layer | Corrosion Resis. | Wear Resis. (micro-m.) | Cling-ingness |
|---|---|---|---|---|---|
| Embodi-ments | A | Ti | 5 | 0.20 | Good |
| | B | TiN | 7 | 0.18 | Good |
| | C | TiC | 8 | 0.05 | Good |
| | D | TiCN | 7 | 0.07 | Good |
| | X | No Coating | 1 | 8.30 | — |
| Reference Examples | Y | SiO2 | 1.1 | 3.40 | Peel Occurred All Over |
| | Z | Cr2O3 | 1.2 | 6.80 | Peel Occurred Partly |

(Embodiment 6)

Nd—Fe—B magnets 1 (the remanent magnetic flux density Br=13 KG, the coercive force iHc=15 KOe) were worked to 3.46 mm in diameter D and 0.7 mm in thickness H2; epoxy-coated to 10–40 micrometers in thickness; inserted in a case 2 formed of 17.2 Cr, 0.53 Mo and balance Fe (wt %) and having an outer diameter D1 of 4.5 mm and a thickness H2 of 1.52 mm; and then covered with a seal member 13 made by fitting a seal center member 15 formed of the same material as that of the case and having a thickness H2 of 0.21 mm in a seal frame member 14 of austenitic stainless steel SUS316L. The width G of each seal frame member was 0.25 mm. Grinding for bead removal resulted in H1=1.5 mm. The resultant magnet assemblies were degreased in an alkaline solution having a pH of 12–14 for 20 minutes as a preparatory process. Then, single-layer coating layers referred to as Nos. A through D as shown in the second table were formed by means of ion plating at a temperature of 200° to 250° C. and a vacuum degree of 5×10$^{-4}$ Torr for 5 to 15 minutes. The coating layers were formed to 2.5 micrometers in thickness on all over the surface of the magnet assemblies. Following the coating layer formation, the magnet assemblies were magnetized in the arrow direction, thus permanent magnet assemblies being obtained.

A coating layer was formed of the same material in the same way as in case of a permanent magnet assembly on the surface of a keeper formed of the same material as that of the case 2 and having a diameter of 4.5 mm and a thickness of 0.8 mm; each of the permanent magnet assemblies was made to absorb the keeper; the force necessary for pulling the keeper perpendicularly apart from the permanent magnet assembly was measured defining the force as the attractive force; and the attractive force of any permanent magnet assembly with a coating layer was found to be 860 gf.

Next, in order to evaluate the corrosion resistance of Nos. A through D, the degree of corrosion resistance was measured varying the test time in a solution of 6% FeCl$_3$+N/20HCl at a test temperature of 35° C. Assuming that the degree of corrosion resistance is one if there is "no coating" (No. X) and the test time is 12 hours, the degrees of corrosion resistance for Embodiments A through D. are shown in Table 2. It is understood from Table 2 that forming a coating layer have an effect of enhancing the corrosion resistance and that the longer the test time becomes, the remarkable the effect becomes.

TABLE 2

| Case and Keeper | Corrosion Resistance | | |
|---|---|---|---|
| Coating Layer | 12 h | 24 h | 48 h |
| A Ti | 7 | 6 | 5 |
| B TiN | 8 | 7 | 5 |
| C TiC | 9 | 8 | 7 |
| D TiCN | 12 | 9 | 7 |
| X No Coating | 1 | 0.7 | 0.1 |

(Embodiment 7)

Permanent magnet assemblies were made in the following way: Nd—Fe—B magnets 1 (the remanent magnetic flux density Br=13 KG, the coercive force iHc=15 KOe) were worked to 3.46 mm in diameter D and 0.7 mm in thickness H2; epoxy-coated to 10–40 micrometers in thickness; inserted in a case 2 formed of ferrite stainless steel SUS430 and having an outer diameter D1 of 4.5 mm and a thickness H2 of 1.52 mm; and then covered with a seal member 13 made by fitting a seal center member 15 formed of the same material as that of the case and having a thickness H3 of 0.21 mm in a seal frame member 14 of austenitic stainless steel SUS316L. The width G of each seal frame member was 0.25 mm. Grinding for bead removal resulted in permanent magnet assemblies with H1=1.5 mm. The resultant magnet assemblies were degreased in an alkaline solution having a pH of 12–14 for 15 minutes as a preparatory process. Then, double-layer coating layers referred to as Nos. E through J as shown in the second table were formed by means of ion plating at a temperature of 200° to 250° C. and a vacuum degree of 2×10$^{-4}$ Torr for 5 to 15 minutes. The coating layers were formed to 2.5 micrometers in total thickness on all over the surface of the magnet assemblies. Following the coating layer formation, the magnet assemblies were magnetized in the arrow direction, thus the permanent magnet assemblies being finished.

Each of the permanent magnet assemblies was made to absorb a keeper formed of the same material as that of the case 2 and having a diameter of 4.5 mm and a thickness of 0.8 mm; the force necessary for pulling the keeper perpendicularly apart from the permanent magnet assembly was measured defining the force as the attractive force; and the attractive force of any permanent magnet assembly with a coating layer was found to be 870 gf.

The resultant permanent magnet assemblies were evaluated in the same way as in the fifth embodiment, and the results are shown in Table 3.

As seen from Table 3, making the coating layers multi-layer structures yielded a higher corrosion resistance. Embodiments E through J showed much smaller wear as compared with Reference Examples Y and Z. Also, the clingingness between the coating layer and the permanent magnet assembly was good.

TABLE 3

|  | No. | Coating Layer I | Coating Layer II | Corrosion Resis. | Wear Resis. (micro-m) | Cling-ingness |
|---|---|---|---|---|---|---|
| Embodi-ments | E | Ti | TiN | 11 | 0.19 | Good |
|  | F | TiN | TiC | 12 | 0.08 | Good |
|  | G | TiC | TiCN | 11 | 0.05 | Good |
|  | H | TiCN | Ti | 10 | 0.14 | Good |
|  | I | Ti | TiC | 13 | 0.12 | Good |
|  | J | TiN | TiCN | 11 | 0.10 | Good |

(Embodiment 8)

Permanent magnet assemblies were made in the following way: Nd—Fe—B magnets 1 (the remanent magnetic flux density Br=13 KG, the coercive force iHc=15 KOe) were worked to 3.46 mm in diameter D and 0.7 mm in thickness H2; epoxy-coated to 10–40 micrometers in thickness; inserted in a case 2 formed of ferrite stainless steel SUS430 and having an outer diameter D1 of 4.5 mm and a thickness H2 of 1.52 mm; and then covered with a seal member 13 made by fitting a seal center member 15 formed of the same material as that of the case and having a thickness H3 of 0.21 mm in a seal frame member 14 of austenitic stainless steel SUS316L. The width G of each seal frame member was 0.25 mm. Grinding for bead removal resulted in permanent magnet assemblies with H1=1.5 mm. The resultant magnet assemblies were degreased in an alkaline solution having a pH of 12–14 for 15 minutes as a preparatory process. Then, triple-layer coating layers referred to as Nos. K through N as shown in the fourth table were formed by means of ion plating at a temperature of 200° to 250° C. and a vacuum degree of $3\times10^{-4}$ Torr for 5 to 15 minutes. The coating layers were formed to 2.5 micrometers in total thickness on all over the surface of the magnet assemblies. Following the coating layer formation, the magnet assemblies were magnetized in the arrow direction, thus the permanent magnet assemblies being finished.

The resultant permanent magnet assemblies were evaluated in the same way as in the fifth embodiment, and the results are shown in Table 4.

As seen from Table 4, making the coating layers multi-layer structures yielded a higher corrosion resistance. Embodiments K through N showed much smaller wear as compared with Reference Examples Y and Z of the fifth embodiment. Also, the clingingness between the coating layer and the permanent magnet assembly was good.

TABLE 4

|  | No. | Coating Layer I | Coating Layer II | Coating Layer III | Corrosion Resis. | Wear Resis. (micro-m.) | Cling-ingness |
|---|---|---|---|---|---|---|---|
| Embodi-ments | K | Ti | TiN | TiC | 13 | 0.18 | Good |
|  | L | TiN | TiC | TiCN | 14 | 0.07 | Good |
|  | M | TiC | TiCN | Ti | 13 | 0.10 | Good |
|  | N | TiCN | Ti | TiN | 15 | 0.19 | Good |

(Embodiment 9)

Permanent magnet assemblies were made in the following way: Nd—Fe—B magnets 1 (the remanent magnetic flux density Br=13 KG, the coercive force iHc=15 KOe) were worked to 3.46 mm in diameter D and 0.7 mm in thickness H2; epoxy-coated to 10–40 micrometers in thickness; inserted in a case 2 formed of ferrite stainless steel SUS430 and having an outer diameter D1 of 4.5 mm and a thickness H2 of 1.52 mm; and then covered with a seal member 13 made by fitting a seal center member 15 formed of the same material as that of the case and having a thickness H3 of 0.21 mm in a seal frame member 14 of austenitic stainless steel SUS316L. The width G of each seal frame member was 0.25 mm. Grinding for bead removal resulted in permanent magnet assemblies with H1=1.5 mm. The resultant magnet assemblies were degreased in an alkaline solution having a pH of 12–14 for 20 minutes as a preparatory process. Then, triple-layer coating layers referred to as Nos. O through R as shown in the fifth table were formed by means of ion plating at a temperature of 200° to 250° C. and a vacuum degree of $1\times10^{-4}$ Torr for 5 to 15 minutes. The coating layers were formed to 2.5 micrometers in total thickness on all over the outer surface of the magnet assemblies. Following the coating layer formation, the magnet assemblies were magnetized in the arrow direction, thus the permanent magnet assembly Nos. O through R being finished.

The resultant permanent magnet assemblies were evaluated in the same way as in the fifth embodiment, and the results are shown in Table 5.

As seen from Table 5, making the coating layers multi-layer structures yielded a higher corrosion resistance. Embodiments O through R showed much smaller wear as compared with Reference Examples Y and Z of the fifth embodiment. Also, the clingingness between the coating layer and the permanent magnet assembly was good.

TABLE 5

|  | No. | Coating Layer I | Coating Layer II | Coating Layer III | Coating Layer IV | Corrosion Resis. | Wear Resis. (micro-m.) | Cling-ing-ness |
|---|---|---|---|---|---|---|---|---|
| Embodi-ments | O | Ti | TiN | TiC | TiCN | 16 | 0.06 | Good |
|  | P | TiN | TiC | TiCN | Ti | 15 | 0.09 | Good |
|  | Q | TiC | TiCN | Ti | TiN | 16 | 0.07 | Good |
|  | R | TiCN | Ti | TiN | TiC | 17 | 0.05 | Good |

(Embodiment 10)

Permanent magnet assemblies were made in the following way: Nd—Fe—B magnets 1 (the remanent magnetic flux density Br=13 KG, the coercive force iHc=15 KOe) were worked to 3.06 mm in diameter D2 and 0.7 mm in thickness H2; epoxy-coated to 10–40 micrometers in thickness; magnetized in the arrow direction; inserted in a case 2 formed of ferrite stainless steel SUS430 (the saturation magnetic flux density Bs=16 KG) and having an outer diameter D1 of 4.0 mm and a thickness H2 of 1.52 mm; and then covered with a seal member 13 made by fitting a seal center member 15 formed of the same material as that of the case and having a thickness H3 of 0.21 mm in a seal frame member 14 of austenitic stainless steel SUS316L. The width G of each seal frame member was 0.25 mm. Grinding for bead removal resulted in permanent magnet assemblies with H1=1.5 mm. The resultant magnet assemblies were degreased in an alkaline solution having a pH of 12–14 for 15 minutes as a preparatory process. Then, TiC coating layers of the thicknesses as shown in the fifth table were formed on the exterior side faces 2b of each magnetic material case, the exterior bottom face 2a of the case and the outside of each shield plate. The coating layers were formed by means of ion plating at a temperature of 200° to 250° C. and a vacuum degree of $2\times10^{-4}$ Torr for 5 to 15 minutes.

Following the coating layer formation, the magnet assemblies were magnetized in the arrow direction; each of the permanent magnet assemblies was made to absorb a keeper formed of the same material as that of the case 2 and having a diameter of 4.0 mm and a thickness of 0.8 mm; the force necessary for pulling the keeper perpendicularly apart from the permanent magnet assembly was measured defining the force as the attractive force. The results are shown in Table 6.

It is seen from Table 6 that a practically sufficient attractive force is obtained if the thickness of the coating layer is in a range from 1 to 20 micrometers, and an excellent attractive force is obtained particularly by making the thickness 1 to 10 micrometers.

TABLE 6

|  | Thickness of Coating Layer (micrometers) | attractive force (gf) |
| --- | --- | --- |
| Reference Example | 0 | 720 |
| Embodiments | 0.8 | 712 |
|  | 2.5 | 698 |
|  | 7.0 | 576 |
|  | 11.0 | 500 |
|  | 18.0 | 374 |
| Reference Example | 22.0 | 330 |

As is apparent from descriptions in conjunction with the above illustrative embodiments, if a permanent magnet assembly is to be embedded in a denture base in a limited space where a crown of a front tooth used to be, the attractive force between the permanent magnet assembly and a keeper can be so kept as to be sufficiently satisfactory as a force for retaining the denture according to the invention even if the permanent magnet assembly is miniaturized, so that the denture becomes hard to break. Furthermore, the invention provides a clinically-safe magnetic denture retainer because it is possible to completely prevent metal ions from dissolving out by coating the surface of such a retainer as a permanent magnet assembly.

We claim:

1. A denture-supporting permanent magnet assembly comprising: a case formed of a magnetic material and having an opening at one end; a permanent magnet housed in said case; and a seal member, having a magnetic part and a nonmagnetic part, for sealing said opening of said case, wherein said case is made of a corrosion-resistant magnetic material having a composition of 15.5–18.5 wt % Cr, balance iron and impurities and said seal member comprises:

a seal frame member made of a nonmagnetic material; and a seal center member made of a corrosion-resistant magnetic material which contains 15.5–18.5 wt % Cr, balance iron and impurities.

2. The assembly according to claim 1, wherein said permanent magnet is a Nd—Fe—B system magnet having a corrosion-resistant film of 10 to 40 micrometers on the surface.

3. The assembly according to claim 1, wherein the assembly has a coating layer on its surface formed of a material selected from the group consisting of Ti and a Ti compound.

4. The assembly according to claim 3, wherein said Ti compound comprises at least one of TiN, TiC and TiCN.

5. The assembly according to claim 4, characterized in that said coating layer has a multi-layer structure comprising a plurality of sub-layers different in composition.

6. The assembly according to claim 5, characterized in that each of said sub-layers is formed of one of Ti and a Ti compound.

7. A denture-supporting magnet assembly comprising: a case formed of a nonmagnetic material and having an opening at one end; a permanent magnet housed in said case; and a seal member for sealing said opening of said case,
wherein said assembly has a coating layer on its surface formed of a material selected from the group consisting of Ti and a Ti compound.

8. A denture-supporting permanent magnet assembly according to claim 7, characterized in that the thickness of said coating layer is from 1 to 20 micrometers.

9. A denture-supporting permanent magnet assembly comprising: a case formed of one of a magnetic and a nonmagnetic material and having an opening at one end; a permanent magnet housed in said case; and a seal member for sealing up said opening of said case, wherein said case is crowned with a material selected from the group consisting of Ti and a Ti compound.

10. A denture-supporting keeper characterized in that said keeper comprises:

a keeper main body formed of a magnetic material; and wherein said keeper main body has a coating layer on its surface formed of a material selected from the group consisting of Ti and a Ti compound.

11. The keeper according to claim 10, characterized in that said keeper main body is formed of a magnetic material containing in weight-%: 15.5–18.5 Cr; balance iron; and impurities.

12. The keeper according to claim 10 or 11, characterized in that the thickness of said coating layer is from 1 to 20 micrometers.

13. A denture-supporting keeper characterized in that said keeper comprises:

a keeper main body formed of a magnetic material;

a handle formed of selected one of Ti and a Ti compound; and a coating layer formed of selected one of Ti and a Ti compound on the surface of said keeper main body.

14. A denture-supporting attachment comprising: a denture-supporting permanent magnet assembly comprising a case formed of one of a magnetic and a nonmagnetic material and having an opening at one end, a permanent magnet housed in said case, and a seal member for sealing up said opening of said case; and a denture-supporting keeper formed of a magnetic material, wherein said denture-supporting permanent magnet assembly has a coating layer on its surface formed of a material selected from the group consisting of Ti and a Ti compound.

15. The attachment according to claim 14, characterized in that said denture-supporting keeper comprises:

a keeper main body formed of a magnetic material; and wherein said keeper main body has a coating layer on its surface formed of a material selected from the group consisting of Ti and a Ti compound.

16. The attachment according to claim 14 or 15, wherein said denture-supporting keeper has a handle formed of a material selected from the group consisting of Ti and a Ti compound.

* * * * *